United States Patent [19]
Chase et al.

[11] Patent Number: 4,706,267
[45] Date of Patent: Nov. 10, 1987

[54] DEFECT DETECTOR FOR CORD REINFORCED TIRE FABRIC

[75] Inventors: Lee M. Chase; David Sudikoff, both of Cupertino, Calif.

[73] Assignee: Measurex Corporation, Cupertino, Calif.

[21] Appl. No.: 814,731

[22] Filed: Dec. 30, 1985

[51] Int. Cl.⁴ ................... G01B 15/06; G01N 23/02
[52] U.S. Cl. ................................. 378/61; 378/58
[58] Field of Search ............... 378/61, 58; 356/386, 356/387; 250/358.1, 359.1, 360.1

[56] References Cited
U.S. PATENT DOCUMENTS 3,497,693  2/1970  Duttschmid et al. ............ 250/360.1
3,727,054  4/1973  Herrick .................................. 378/61

FOREIGN PATENT DOCUMENTS 2364653  6/1975  Fed. Rep. of Germany ........ 378/61

Primary Examiner—Carolyn E. Fields
Assistant Examiner—Joseph A. Hynds
Attorney, Agent, or Firm—Spensley Horn Jubas & Lubitz

[57] ABSTRACT

A system for detecting missing or crossed cords in cord reinforced tire fabric. The entire width of the fabric as it is being made is scanned by a highly collimated X-ray source and a sensor. A change in the amount of X-ray radiation penetrating the fabric indicates the presence of the cords. A counter which counts at a fixed rate is gated on during the time that a cord's presence is detected. The total count in a small section of the fabric, called a slice, is proportional to the number of strands in the slice. Since the counting rate is relatively high with respect to the scan time, the system can easily detect missing or overlapping cords.

5 Claims, 5 Drawing Figures

DEFECT DETECTOR FOR CORD REINFORCED TIRE FABRIC

BACKGROUND OF THE INVENTION

This invention relates to the detection of defects in the cording of cord reinforced tire fabric and in particular, the detection of missing or overlapping cords. The invention is particularly useful for detecting defects in steel cord reinforced fabric, but also can be used to detect defects in fabric having other types of reinforcing cords, so long as the radiation absorbtion coefficient of the cord is not the same as for rubber. For convenience, the following specification describes the invention in connection with steel reinforced fabric.

Tire fabric for vehicle tires is usually made in a continuous calendering process wherein rubber latex is calendered onto a plurality of reinforcing strands so as to form a sandwich having a strand core with a layer of rubber on each side. In the course of the calendering operation, it is possible for one or more of the strands to be missing or for two strands to overlap, either of which constitutes a defect. It is also possible for the spacing of the strands to become non-uniform so that the number of strands in a section of fabric is below a required minimum. Since the rubber is opaque, defects must be detected by non-optical means.

There are a number of non-optical ways of detecting the presence of reinforcing strands, and defect detection methods involving scanning the fabric and simply counting the total number of strands have been suggested. This method is not satisfactory since it is important that each small section of the fabric be defect-free, and within a relatively small area of fabric a one strand difference in the predicted count could be caused by the plus/minus one count digitizing error inherent in digital counting systems rather than by a missing cord.

Accordingly, the present invention provides a sensitive cord counting system in which digitization errors do not make the cord count ambiguous.

SUMMARY OF THE INVENTION

Steel cord reinforced tire fabric is typically made in widths of about four feet. It is not sufficient that over the entire width of the fabric there be adequate cord reinforcement, rather, each small section of tire fabric must contain the proper number of cords. To accommodate this requirement, the width of the fabric is divided into small sections called "slices" for purposes of inspection. Each "slice" may be, for example, one inch of width, and it is essential that a certain minimum number of cords exist within each slice. A missing cord or crossed cords within any slice are considered defects and are easily detected by the present invention.

The invented system involves scanning the tire fabric using a highly collimated X-ray beam directed through the fabric. Substantially all of the X-ray energy is absorbed by the steel cord, but a significant part of the energy is transmitted through the rubber portion of the fabric. An X-ray sensor on the other side of the fabric therefore will receive a varying amount of radiation as the fabric is scanned. The X-ray source and the sensor scan the fabric width repeatedly at constant speed detecting the presence of cords. Clock pulses occurring at a relatively high rate are gated to a counter during the time the X-ray source is encountering a steel cord. The total count gated for each "slice" of fabric represents the portion of each slice which contains a cord, and thus is a measure of the number of cords in the slice. Because the system results in many counts per cord, a fractional cord within the slice can be accounted for, and a missing cord results in a substantial decrease in the count.

DETAILED DESCRIPTION OF THE INVENTION

Figure 1:
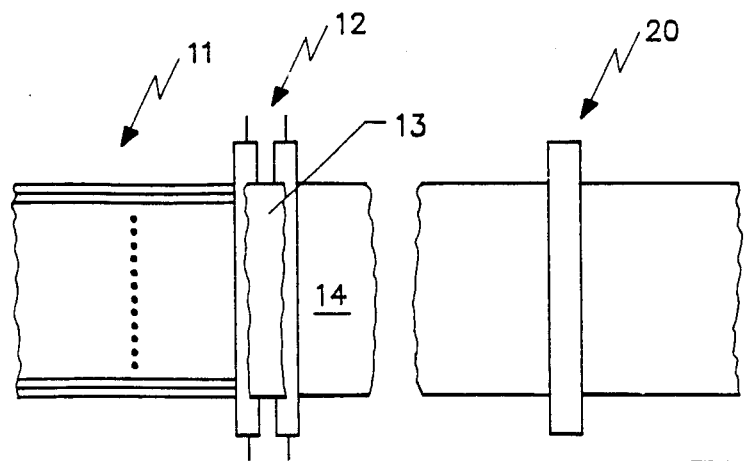
FIG. 1 is a diagrammatic plan view of a steel cord reinforced tire fabric calender which may be used in connection with the present invention.

FIG. 1 shows a highly diagrammatic plan view of a steel cord tire fabric calender such as may be used in connection with the present invention. Steel cord tire fabric is typically made in widths of about four feet and has about 5 to 20 reinforcement cords per inch of width. As shown in FIG. 1, the steel cords 11 enter from the left of the machine and pass under calender rolls 12 which deposit a sheet of latex on top of the travelling cords. The latex pool 13 on top of the rolls 12 is kept replenished by means not shown. A second set of calender rolls (also not shown) are located under the plane of the travelling cords and apply a similar sheet of latex to the under side of the cords. As the sheets of latex are applied, they flow between the cords and coalesce into a single entity. The fabric leaving the rolls is thus a sheet of latex with a core of spaced steel reinforcing cord.

Figure 2:
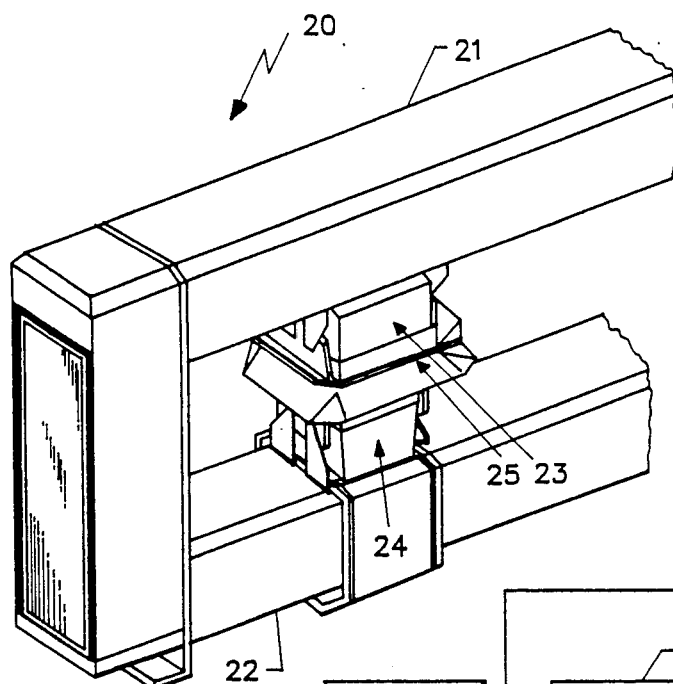
FIG. 2 is a perspective view of a portion of the monitor section of the present invention.

After leaving the calender rolls, and possibly after some further processing, the fabric is passed through a monitor section 20 to determine certain of its characteristics. One characteristic which may be monitored is the proportion of each "slice" of fabric which is occupied by reinforcing cord. A "slice" is a small section of the width of the fabric, commonly about one inch. The monitor section, which holds the sensing portion of the invented apparatus, includes upper and lower traverse beams 21 and 22 as can be seen in FIG. 2. The upper and lower traverse beams are located, as their names imply, over and under the fabric web.

X-ray source head 23 and sensor head 24 are mounted to the upper and lower traverse beams respectively such that they can move back and forth on the beams, with the fabric web passing in the space 25 between them. Means not shown keep the X-ray source and sensor in alignment, and cause both to scan back and forth across the width of the fabric at constant speed. Pulses are generated during the scan to indicate the start of each slice by a start of slice pulse generator 49 coupled to the X-ray source and sensor.

Figure 3:
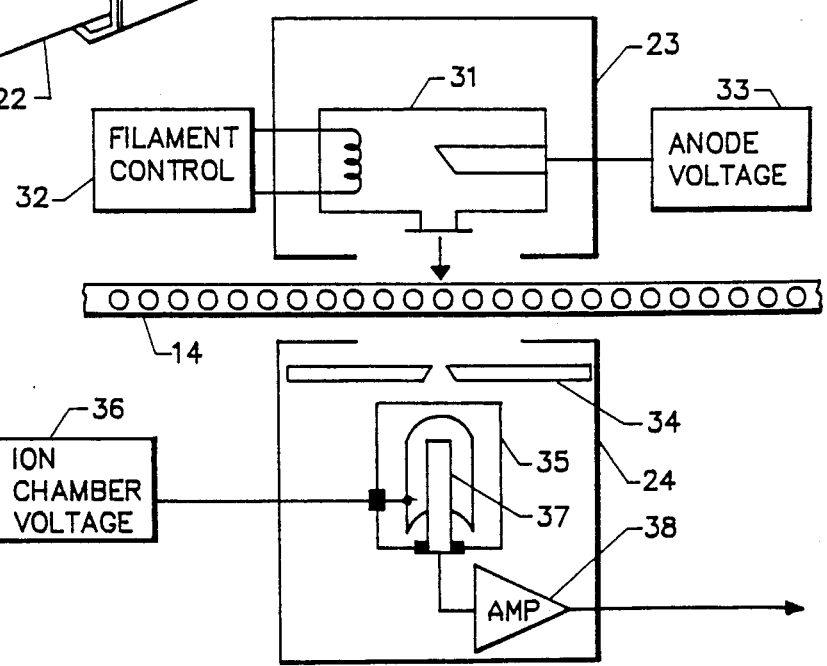
FIG. 3 is a diagrammatic cross sectional view of the X-ray source and sensor of the present invention.

FIG. 3 shows the arrangement of X-ray source head 23 and sensor head 24. X-ray tube 31, energized by filament control 32 and anode voltage source 33, emits a relatively narrow X-ray beam downward through fabric 14 and through aperture slit 34 into ionization chamber 35. The aperture slit width is typically 0.010 inch which provides a narrow beam width and good definition of the edges of the cords. Alternatively, the beam emitted by source 23 could be collimated before it passes through the fabric. Ionization within chamber 35 permits a current to flow from the ionization chamber voltage source 36 to central electrode 37. The operation of ionization chamber detectors for the detection of X-rays is well known so that it is not believed necessary to explain the operation of this portion of the invention in more detail. It is sufficient to note that when one of the steel cords of tire fabric 14 blocks the X-ray beam, the output of amplifier 38 is low, but when only rubber is between the X-ray tube and the ionization chamber the amplifier output is high.

Figure 4:
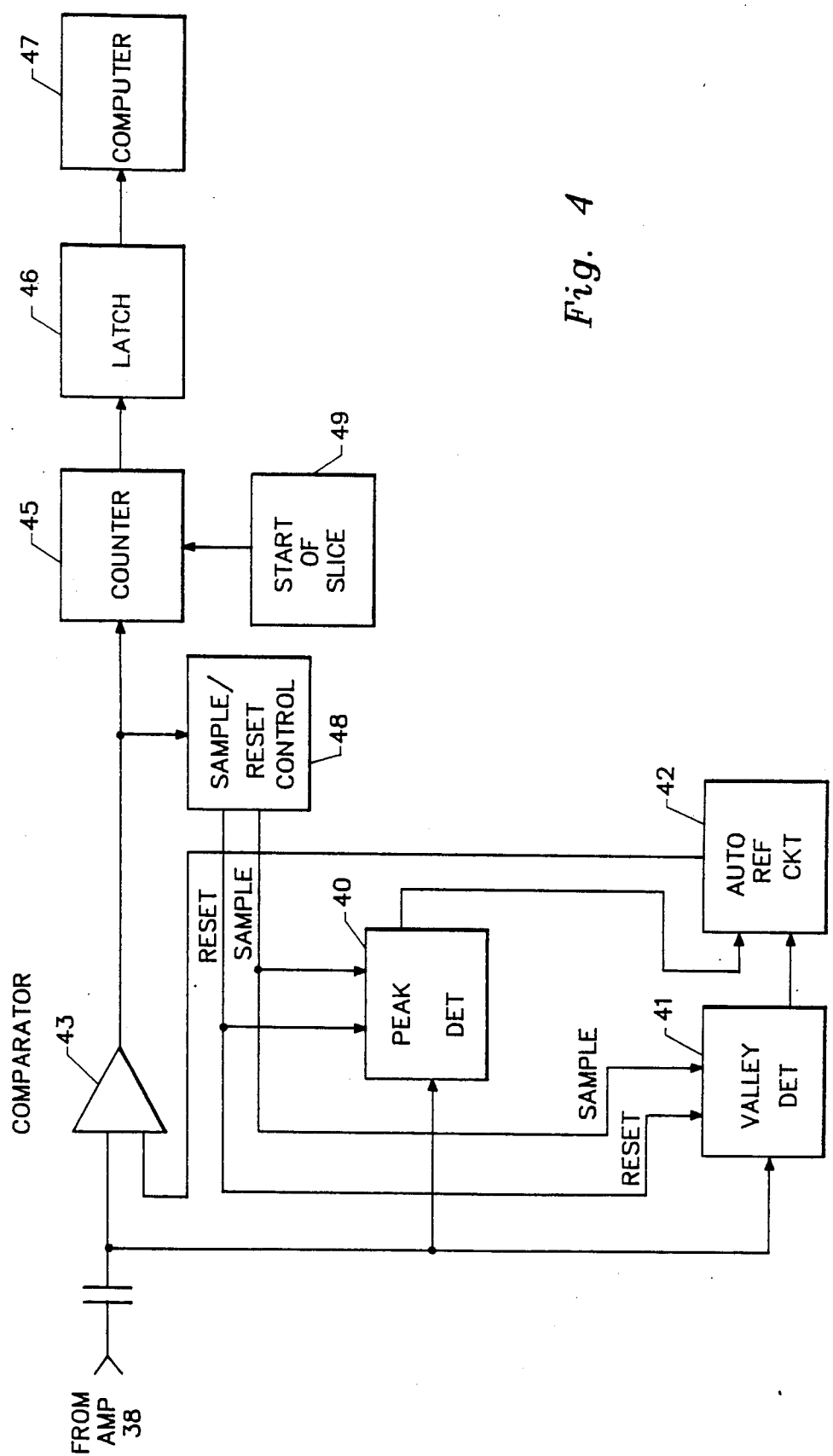
FIG. 4 is a block diagram of the electronic portion of the present invention.
Figure 5:
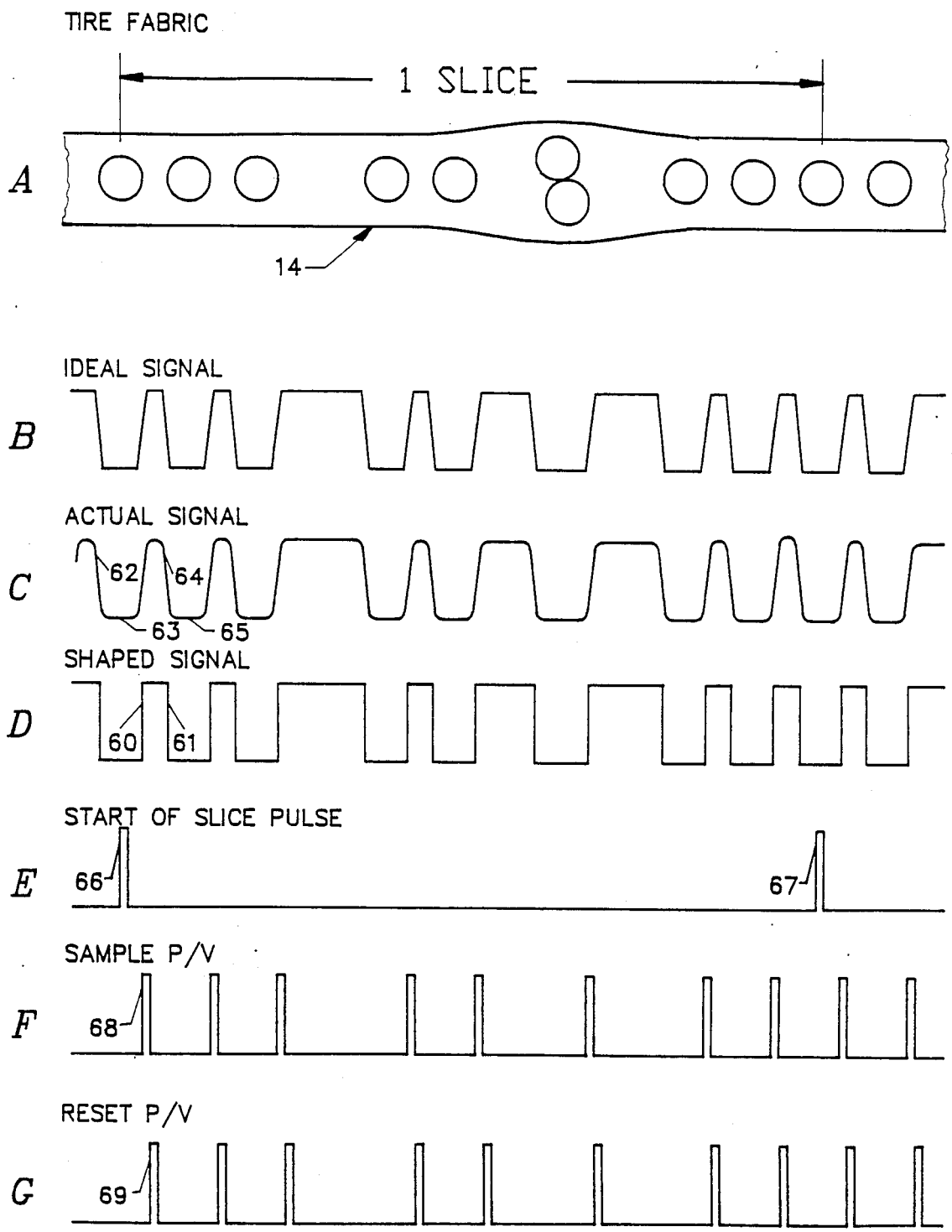
FIG. 5 shows various waveforms generated in the electronic portion.

For purposes of illustration, a small section of tire fabric is shown in FIG. 5 along with waveforms that would be generated by the electronic circuitry of the present invention during a traverse by the sensing elements (23, 24) from left to right. The exemplary section of fabric shown in FIG. 5A is a representative "slice" of fabric which nominally contains 10 cords, but as noted above tire fabric may be encountered which has other cord counts. The section postulated includes one missing cord and a crossover for purposes of illustration. The slice indicated in FIG. 5 is shown starting at the center of a cord, but this is mere happenstance since the pulses which signal the start of a slice are generated by means coupled to the X-ray traverse system, which is not precisely aligned with the cords. The start of slice pulse generator 49 (shown in the block diagram of FIG. 4) delivers one pulse for each slice of travel of the X-ray source and sensor heads (23, 24).

As the X-ray source/sensor 23, 24 traverses the slice of cord illustrated in FIG. 5A, an undulating waveform appears at the output of amplifier 38. Ideally, the waveform is trapezoidal as shown in FIG. 5B, but in actual practice the corners are rounded as shown in FIG. 5C. The slope of the leading and trailing edges of the ideal waveform 5B are due to the finite diameter of the collimated X-ray beam, and the rounded corners of actual waveform 5C arise because of non-uniformities in the beam and the partial X-ray transparency of the cords.

The output of amplifier 38 is fed to peak detector 40 and valley detector 41 (FIG. 4) which hold the maximum and minimum voltages experienced, respectively, until reset. The maximum and minimum voltages held by the peak and valley detectors are fed to the automatic reference circuit 42 whenever the detectors (40, 41) receive a "sample" pulse from the sample/reset control unit 48. In response to an input from the peak and valley detectors, the automatic reference circuit 42 generates a voltage approximately equal to one-half the peak plus valley voltage and couples this voltage to comparator 43 to act as a reference voltage for the comparator. Ideally, the reference voltage is exactly equal to one half the peak plus valley voltage, but since the actual waveform of FIG. 5C may not be perfectly symmetrical, the required reference voltage may not be exactly the ideal voltage. The reference voltage is maintained until another sample pulse causes the voltage to change.

The output of comparator 43 is the shaped signal of waveform 5D. It goes negative when the X-ray source/sensor passes the leading edge of a cord and positive at the trailing edge. The reference voltage may have to be adjusted slightly as noted above so that the transitions in the waveform of FIG. 5D occur when the X-ray beam is centered over a cord edge.

The peak/valley sample and reset pulses are generated in the sample/reset control unit 48 which is driven by the shaped signal (5D). A sample pulse is generated coincident with the positive going edge of the shaped signal voltage (FIG. 5F) followed by a reset pulse (FIG. 5G) sufficiently after the sample pulse to allow the voltages then being held in the peak and valley detectors (40, 41) to be coupled to the auto reference circuit before the peak and valley detectors are reset. After being reset, the peak and valley detectors will store the maximum and minimum values of waveform 5C which occur before the next sample pulse, e.g. voltages 64 and 65 of FIG. 5C after reset pulse 69.

The output of comparator 43 is coupled to counter 45 in such a way that counter 45 counts pulses from an internal oscillator so long as the output of comparator 43 is negative. The oscillator in counter 45 should be set to a rate that is relatively high with respect to the time of travel between cords, for example, 100 counts per cord diameter.

The occurrence of a start of slice pulse (66 in FIG. 5E) latches the count of counter 45 into latch 46 and resets the counter to zero. The count in latch 46 at any instant can be seen to be equal to the total count of counter 45 during the preceding slice interval. It is proportional to the total fraction of the slice occupied by cords.

The operation of the system can be understood by reference to FIG. 5. For purposes of the explanation, assume that the counter 45 counts at a rate of 100 counts during the time that the X-ray source and sensor travel a distance equal to one cord diameter. The X-ray source and sensor are assumed to travel from left to right. The slice starting pulse 66 (5E) is seen occurring (in this example) when the X-ray source and sensor are exactly centered on a cord. At this time, the counter 45 is reset, and it starts counting from zero. When the shaped signal goes positive (at 60), there will be 50 counts on the counter since the X-ray source and sensor have travelled a distance equal to one-half cord diameter. The count remains at 50 until the shaped signal goes negative again when the next cord is encountered by the X-ray source/sensor (at 61).

In addition to stopping the counter, the positive going edge of the shaped signal causes a sample pulse to be directed to the peak and valley detectors transferring the maximum positive and negative voltages encountered during the previous cycle (62, 63) to the auto reference circuit 42, which in turn readjusts the comparator 43 reference voltage. After the peak/valley detectors have been sampled, they are reset by pulse 69 so as to be able to detect the maximum and minimum sensor output voltages during the next cycle of sensor output (64, 65).

At the next negative going shaped signal transition (61), counter 45 resumes counting. One hundred more counts will be added to the counter during the traverse of the next cord. This process continues, with the count in counter 45 increasing during the traverse of each cord, until the next start of slice pulse (67), at which time the count in counter 45 is latched into latch 46 and the counter reset to zero for the next slice.

In the example shown in FIG. 5, the fourth cord is missing and the seventh and eighth cords are crossed. Because of the position of the seventh and eighth cords in the slice as shown, the count added during the traverse of this area will be about $1\frac{1}{4}$ times a single cord, or about 125 counts. The total count during the slice as illustrated, then, will be 825. Had there been no crossover or missing cords, the count would have been 1000. If the only defect had been missing cord, the count would have been 900 and if only the crossover had occurred, the count would have been 925. The missing cord and crossover are thus seen to be easily discernable and digitization errors cannot cause the results to be ambiguous. The total count for a slice with no strands missing can vary somewhat due to the end cord being out of position, but this variation will be normally less than plus or minus 50 counts (assuming the counting rate of the example). The decrease in count due to a defect will thus be sufficient to allow alarms to be set without fear of false tripping.

The count in latch 46 is shown being coupled to computer 47 where the data can be displayed, recorded or used to trigger alarms in accordance with well known procedures. None of these are shown in detail since processing of digital data such as is latched into latch 46 is well known to workers in the art.

What has been described is a presently preferred embodiment of a system for detecting missing wire strands in wire cord reinforced tire fabric. It should be understood that while a presently preferred embodiment of the invention has been disclosed, various modifications within the spirit of the invention will no doubt occur to those skilled in the art and such modifications are intended to be covered by the following claims.

We claim:

1. A system for detecting missing or overlapping cords in cord reinforced tire fabric which comprises:
    (a) a radiation source for providing a collimated beam of radiation through said tire fabric, said radiation being such that a greater amount of radiation will penetrate through the rubber of said fabric than through the cord of said fabric;
    (b) a sensor aligned with said collimated beam of radiation for detecting said radiation and generating an electrical signal in response thereto;
    (c) means for causing said radiation source and said sensor to scan across a section of said tire fabric at a predetermined speed;
    (d) means responsive to said electrical signal generated by said sensor for providing a timing signal when said sensor bears a predetermined relationship to each edge of the cords in said fabric; and
    (e) means responsive to said timing signals. during a predetermined scan distance for measuring the total time a cord is between said radiation source and said sensor.

2. The system of claim 1 where said radiation source is an X-ray source.

3. The system of claim 1 where said means for providing a timing signal includes:
    (a) means for detecting successive maximum and minimum values of said electrical signal;
    (b) means for providing a reference voltage dependent on said maximum and minimum voltages; and
    (c) comparator means for generating one of said timing signals each time said electrical signal equals said reference voltage.

4. The system of claim 3 where said reference voltage has a magnitude equal to one-half of the sum of said maximum and minimum values of said electrical signal.

5. The system of claim 1 where said means responsive to said timing signals includes:
    (a) counter means for counting at a predetermined rate;
    (b) gating means for causing said counter to count during the time a cord is between said radiation source and said sensor; and
    (c) reset means for resetting the count of said counter to a predetermined number each time said radiation source and sensor have scanned a predetermined distance.

* * * * *